United States Patent
Cheresh et al.

(10) Patent No.: US 7,125,849 B2
(45) Date of Patent: Oct. 24, 2006

(54) PEPTIDE-BASED ANGIOGENESIS INHIBITORS AND METHODS OF USE THEREOF

(75) Inventors: David A. Cheresh, Encinitas, CA (US); John Hood, Solana Beach, CA (US); Martin A. Schwartz, Poway, CA (US); William B. Kiosses, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 233 days.

(21) Appl. No.: 10/341,815

(22) Filed: Jan. 14, 2003

(65) Prior Publication Data

US 2004/0138133 A1    Jul. 15, 2004

(51) Int. Cl.
*A61K 38/10* (2006.01)
*A61K 38/08* (2006.01)
*C07K 7/08* (2006.01)

(52) U.S. Cl. .......................... 514/13; 514/14; 514/15; 514/16; 514/17; 530/327; 530/328; 530/329

(58) Field of Classification Search .................. None
See application file for complete search history.

(56) References Cited

U.S. PATENT DOCUMENTS 6,660,843 B1 * 12/2003 Feige et al. .............. 530/391.7

OTHER PUBLICATIONS

Kiosses et al., Circulation Research 2002, vol. 90, pp. 697-702.*
Kelly et al., Biochemistry 2001, Vo. 40, pp. 14376-14383.*

* cited by examiner

*Primary Examiner*—B. Dell Chism
(74) *Attorney, Agent, or Firm*—Olson & Hierl, Ltd.

(57) ABSTRACT

Angiogenesis inhibitors and methods of use thereof are disclosed. The inhibitors are substantially pure oligopeptides consisting essentially of 7–20 amino acid residues and comprising a proline-rich sequence of five amino acid residues PPXPP, SEQ ID NO: 1, wherein X is an amino acid residue selected from the group consisting of alanine, glycine, serine, threonine, valine, leucine and methionine. In a preferred embodiment, the proline-rich polypeptide is covalently bound to a transport molecule such as a Tat-derived transport polypeptide.

12 Claims, 5 Drawing Sheets

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: PAK-1 proline-rich binding site analog
<220> FEATURE:
<221> NAME/KEY: VARIANT
<222> LOCATION: 3
<223> OTHER INFORMATION: Xaa=Ala, Gly, Ser, Thr, Leu, or Met

<400> SEQUENCE: 1

Pro Pro Xaa Pro Pro
 1               5

<210> SEQ ID NO 2
<211> LENGTH: 13
<212> TYPE: PRT
<213> ORGANISM: HOMO SAPIENS

<400> SEQUENCE: 2

Lys Pro Pro Ala Pro Pro Met Arg Asn Thr Ser Thr Met
 1               5                   10

<210> SEQ ID NO 3
<211> LENGTH: 12
<212> TYPE: PRT
<213> ORGANISM: Artificial Sequence
<220> FEATURE:
<223> OTHER INFORMATION: Tat-derived transport polypeptide
<300> PUBLICATION INFORMATION:
<310> PATENT DOCUMENT NUMBER: US 6,316,003
<311> PATENT FILING DATE: 1994-04-28
<312> PUBLICATION DATE: 2001-11-13

<400> SEQUENCE: 3

Tyr Gly Arg Lys Lys Arg Arg Gln Arg Arg Arg Gly
 1               5                   10

<210> SEQ ID NO 4
<211> LENGTH: 25
<212> TYPE: PRT
<213> ORGANISM: Artificial Sequence
<220> FEATURE:
<223> OTHER INFORMATION: fusion protein fragment

<400> SEQUENCE: 4

Tyr Gly Arg Lys Lys Arg Arg Gln Arg Arg Arg Gly Lys Pro Pro Ala
 1               5                   10                  15

Pro Pro Met Arg Asn Thr Ser Thr Met
                20                  25

<210> SEQ ID NO 5
<211> LENGTH: 25
```

-continued

```
<212> TYPE: PRT
<213> ORGANISM: Artificial Sequence
<220> FEATURE:
<223> OTHER INFORMATION: fusion protein fragment

<400> SEQUENCE: 5

Tyr Gly Arg Lys Lys Arg Arg Gln Arg Arg Arg Gly Lys Ala Gly Ala
 1               5                  10                  15

Pro Pro Met Arg Asn Thr Ser Thr Met
            20                  25
```

PEPTIDE-BASED ANGIOGENESIS INHIBITORS AND METHODS OF USE THEREOF

STATEMENT OF GOVERNMENT RIGHTS

This invention was made with U.S. government support under Contract No. HL 57900, CA 50286, CA 45726, and CA 78045 from the National Institutes of Health. The U.S. government has certain rights to this invention.

FIELD OF THE INVENTION

This invention relates to peptide-based angiogenesis inhibitors. More particularly this invention relates to peptide-based angiogenesis inhibitors containing specific proline-rich amino acid sequences. This invention also relates to methods of using peptide-based angiogenesis inhibitors to inhibit blood vessel formation (angiogenesis) in a vertebrate organism.

BACKGROUND OF THE INVENTION

Angiogenesis is the process by which new blood vessels form. In response to specific chemical signals, capillaries sprout from existing vessels, eventually growing in size as needed by the organism. Initially, endothelial cells, which line the blood vessels, divide in a direction orthogonal to the existing vessel, forming a solid sprout. Adjacent endothelial cells then form large vacuoles and the cells rearrange so that the vacuoles orient themselves end to end and eventually merge to form the lumen of a new capillary (tube formation).

Angiogenesis is stimulated by a number of conditions, such as in response to a wound, and accompanies virtually all tissue growth in vertebrate organisms such as mammals. Angiogenesis also plays a role in certain disease states such as diabetic retinopathy and certain cancers. The growth of tumors, for example, requires blood vessel growth to provide oxygen and nutrients to the growing tumor tissue.

Angiogenesis may be arrested or inhibited by interfering with the chemical signals that stimulate the angiogenic process. For example, angiogenic endothelial cells produce proteases to digest the basal lamina that surround the blood vessels, thus clearing a path for the new capillary. Inhibition of these proteases, or their formation, can prevent new vessels from forming. Likewise, the endothelial cells proliferate in response to chemical signals. Particularly important proliferation signals include the vascular endothelial growth factor (VEGF), and the fibroblast growth factor (FGF) families of proteins. VEGF has been shown to be involved in vascularization of certain tumors. Interference with these proliferation signaling processes can also inhibit angiogenesis.

Kiosses et al. *J. Cell Biol.*, 1999, 147:831–843 (hereinafter "Kiosses et al."), have identified the protein kinase p65 PAK1 (PAK-1) as a potential modulator of endothelial cell migration. PAK-1 is a 65 kD serine/threonine kinase that serves as a direct effector of Rac and Cdc42. The downstream function of PAK-1 is complex, but it is clearly implicated in regulation of the actin cytoskeleton and cell migration. Kiosses, et al. also reported that expression of dominant negative PAK-1 strongly inhibited growth factor-induced endothelial cell movement. The inhibition appeared to be mediated by a decrease in contractility, and it was suggested that PAK-1 plays a role in myosin-dependent contraction and detachment of the rear of the cell. This study also mapped the inhibitory effect of dominant negative PAK-1 to a single, 74 amino acid construct having a 12 amino acid, proline-rich sequence near the amino-terminus of the protein. This sequence was reported by Lu et al., *Curr. Biol.*, 1996, 7:85–94, to bind the SH3 domain from the adapter protein Nck and has been proposed to target PAK-1 to the cell membrane via an interaction with Nck.

There is an ongoing need for effective methods of inhibiting angiogenesis. The present invention provides a method of inhibiting angiogenesis in a vertebrate organism using proline-rich oligopeptides, which are synthetic polypeptides containing proline-rich amino acid sequences that specifically target proliferating endothelial cells, inhibiting cell migration processes that are necessary for blood vessel formation.

SUMMARY OF THE INVENTION

A method of inhibiting angiogenesis in a vertebrate organism is provided, which comprises administering to the vertebrate organism an angiogenesis inhibiting effective amount of a pharmaceutical composition comprising a proline-rich oligopeptide (PRO), which is a 7–20 amino acid oligopeptide comprising at least one amino acid sequence PPXPP (SEQ ID NO: 1) wherein X is alanine, glycine, serine, leucine, or methionine. The remaining amino acid residues can be any amino acid residue. In a preferred embodiment, the amino acid sequence PPXPP (SEQ ID NO: 1) is included in the first 7 amino acids of the oligopeptide.

Preferably, the PRO compounds are covalently bound to a transport molecule, e.g., a Tat-derived transport polypeptide, such as those disclosed by Frankel et al. U.S. Pat. No. 6,316,003 (herein after "Frankel et al."), the relevant disclosures of which are incorporated herein by reference. The transport molecules can facilitate transport of polypeptides through the cell membrane into the cytoplasm, thereby enabling delivery of the inventive angiogenesis inhibitor into the cell without microinjection or transfection.

The PRO inhibitors of the present invention provide an effective treatment for angiogenesis related diseases such as ocular neovascular diseases, neovascular glaucoma, diabetic retinopathy, retrolental fibroplasia, hemangiomas, angiofibromas, psoriasis, osteoarthritis, rheumatoid arthritis, and to control solid tumor growth, such as, e.g. breast, prostate, melanoma, renal, colon, cervical cancer and the like; and metastasis thereof.

BRIEF DESCRIPTION OF THE DRAWINGS

In the Drawings, FIG. 1 (top row) depicts the sequence of a preferred Tat-PRO inhibitor of the present invention, SEQ ID NO:4, and (bottom row) the sequence of a non-inhibitory analog thereof, SEQ ID NO: 5.

DETAILED DESCRIPTION OF PREFERRED EMBODIMENTS

Figure 1:
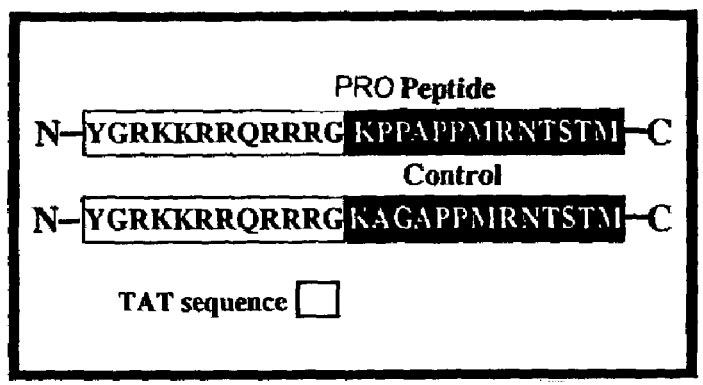

The term "amino acid", as used herein and in the appended claims, refers to a monomeric unit of a polypeptide or protein. The twenty common protein amino acids (L-isomers) are: alanine ("Ala" or "A"), arginine ("Arg" or "R"), asparagine ("Asn" or "N"), aspartic acid ("Asp" or "D"), cysteine ("Cys" or "C"), glutamine ("Gln" or "Q"), glutamic acid ("Glu" or "E"), glycine ("Gly" or "G"), histidine ("His" or "H"), isoleucine ("Ile" or "I"), leucine ("Leu" or "L"), lysine ("Lys" or "K"), methionine ("Met" or "M"), phenylalanine ("Phe" or "F"), proline ("Pro" or "P"), serine ("Ser" or "S"), threonine ("Thr" or "T"), tryptophan ("Trp" or "W"), tyrosine ("Tyr" or "Y") and valine ("Val" or "V"). The term amino acid, as used herein, also includes analogs of amino acids, as well as the D-isomers of the amino acids and their analogs.

The terms "chemical cross-linking" and "coupling" refer to the formation of a covalent bond between two or more pre-formed molecules.

The term "genetic fusion" means the formation of a co-linear, covalent linkage between two or more polypeptides, via their polypeptide backbones, through genetic expression of a DNA molecule encoding both polypeptides linked together as a single molecule.

The terms "transport molecule" and "transport polypeptide", as used herein and in the appended claims, refer to molecule, such as a polypeptide, which is capable of delivering a covalently attached PRO across a cell membrane and into the cytoplasm, e.g., a Tat-derived transport polypeptide as disclosed by Frankel et al. supra.

In a method aspect of the present invention, a method of inhibiting angiogenesis in a vertebrate organism is provided, which comprises administering to the vertebrate organism an angiogenesis inhibiting effective amount of a pharmaceutical composition comprising a proline-rich oligopeptide (PRO), which contains 7–20 amino acid residues and comprising at least one amino acid sequence PPXPP (SEQ ID NO: 1) wherein X is A, G, S, T, L, or M. The remaining amino acid residues can be the residues of any amino acid.

In one preferred method aspect, angiogenesis is inhibited in a vertebrate organism, such as a mammal, by administering to the vertebrate organism an angiogenesis inhibiting effective amount of pharmaceutical composition comprising a PRO, which is a 13 amino acid oligopeptide in which the first 7 amino acid residues from the amino terminus comprise the amino acid sequence PPXPP (SEQ ID NO: 1), where X is A, G, S, T, L, or M, and the remaining amino acid residues can be independently selected from known amino acids. Most preferably X is A. A particularly preferred PRO has the amino acid sequence KPPAPPMRNTSTM (SEQ ID NO: 2).

In another preferred method aspect, a method of inhibiting angiogenesis in a vertebrate organism is provided, which comprises administering to the vertebrate organism an angiogenesis inhibiting effective amount of a pharmaceutical composition comprising a PRO that is covalently bound to a membrane transport facilitator (transport molecule), in which the PRO is a 7–20 amino acid oligopeptide comprising at least one amino acid sequence PPXPP (SEQ ID NO: 1), wherein X is A, G, S, T, L, or M. The transport molecule is preferably covalently bound to the amino terminus of the PRO. Preferably the transport molecule is a Tat-derived transport polypeptide as disclosed by Frankel et al., more preferably, the transport molecule is a polybasic Tat-derived polypeptide, most preferably the transport molecule is a polypeptide having the amino acid sequence YGRKKRRQRRRG (SEQ ID NO: 3).

The present invention also provides a method of treating a vertebrate organism having an angiogenesis-related disease comprising the step of administering to a vertebrate organism in need of such treatment an angiogenesis inhibiting effective amount of pharmaceutical composition comprising an inhibitor, which is a PRO consisting essentially of 7–20 amino acid residues, and which PRO comprises at least one sequence of amino acid residues PPXPP (SEQ ID NO: 1), wherein X is an amino acid residue selected from the group consisting of A, G, S, T, L, and M.

In another preferred method aspect, a method of treating a vertebrate organism having an angiogenesis-related disease is provided, which comprises administering to a vertebrate organism in need of such treatment an angiogenesis inhibiting effective amount of a pharmaceutical composition comprising an inhibitor, which is a PRO that is covalently bound to a transport molecule, in which the PRO is a 7–20 amino acid oligopeptide comprising at least one amino acid sequence PPXPP (SEQ ID NO: 1), wherein X is an amino acid residue selected from the group consisting of A, G, S, T, L, and M. The transport molecule is preferably covalently bound to the amino terminus of the PRO. Preferably the transport molecule is a Tat-derived transport polypeptide as disclosed by Frankel et al., more preferably, the transport molecule is a polybasic Tat-derived polypeptide, most preferably the transport molecule is a polypeptide having the amino acid sequence YGRKKRRQRRRG (SEQ ID NO: 3).

In the method aspects of the present invention, the vertebrate organism is preferably a mammal, most preferably a human. A preferred angiogenesis inhibitor is a polypeptide consisting essentially of 7–20 amino acid residues, and including at least one amino acid sequence PPXPP (SEQ ID NO: 1), in which X is A, G, S, T, L, or M, and in which an amino acid sequence of SEQ ID NO: 1 is included in the first 7 amino acid residues of the oligo peptide (counting from the N-terminus of the oligopeptide). A particularly preferred angiogenesis inhibitor useful in the methods of the present invention is a Tat-PRO conjugate polypeptide having a proline rich 7–20 amino acid residue segment including at least one amino acid sequence SEQ ID NO: 1, covalently bound, at its N-terminus to the carboxyl terminus of a Tat-derived transport oligopeptide of SEQ ID NO: 2, by a peptide bond, i.e.,

YGRKKRRQRRRGKPPAPPMRNTSTM (SEQ ID NO: 4).

Diseases treatable by the methods of the present invention include, but are not limited to, ocular neovascular diseases such as neovascular glaucoma and diabetic retinopathy, retrolental fibroplasia, hemangiomas, angiofibromas, psoriasis, osteoarthritis, rheumatoid arthritis, and to control solid tumor growth, such as, e.g. breast, prostate, melanoma, renal, colon, cervical cancer and the like; and metastasis thereof.

Generally, an angiogenesis inhibiting effective amount of a PRO inhibitor of the present invention is at least about 10 µg/kg body weight and, in most cases, not in excess of about 8 mg/kg body weight per day. Preferably the dosage is in the range of about 10 µg/kg body weight to about 1 mg/kg body weight daily. One of skill in the medical arts would be capable of determining the optimum effective therapeutic dosage of a PRO of the present invention, taking into account the particular patient, inhibitor, disease state, and other factors that are well known in the medical arts.

The present invention also provides pharmaceutical compositions comprising a PRO of the present invention in a pharmaceutically acceptable carrier. The pharmaceutical compositions of this invention can be used for therapeutic or prophylactic applications, and can embodied be in a variety of physical forms. These forms include, for example, solid, semi-solid, and liquid dosage forms, such as tablets, pills, powders, liquid solutions or suspensions, aerosols, liposomes, suppositories, injectable and infusible solutions and sustained release forms. The preferred form depends on the intended mode of administration and the therapeutic or prophylactic application.

According to this invention, a selected PRO compound or a conjugate of a PRO with a transport molecule such as a Tat-derived transport polypeptide, can be administered by conventional routes of administration, such as parenteral, subcutaneous, intravenous, intramuscular, intralesional, intrastemal, intracranial or aerosol routes. Topical routes of administration can also be used, with application of the compositions locally to a particular part of the body (e.g., skin, lower intestinal tract, vagina, rectum) where appropriate. The pharmaceutical compositions also preferably include conventional pharmaceutically acceptable carriers and adjuvants that are known to those of skill in the art.

Generally, the pharmaceutical compositions of the present invention can be formulated and administered using methods and compositions similar to those used for pharmaceutically important polypeptides such as, for example, alpha interferon. It will be understood by those of skill in the art that conventional doses will vary depending upon the particular PRO or transport molecule-PRO conjugate, as well as the patient's health, weight, age, sex, the condition or disease, and the desired mode of administration.

The pharmaceutical compositions of this invention include pharmacologically appropriate carriers, adjuvants and vehicles. In general, these carriers include aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. In addition, intravenous vehicles can include fluid and nutrient replenishers, and electrolyte replenishers, such as those based on Ringer's dextrose. Preservatives and other additives can also be present, such as, for example, antimicrobials, antioxidants, chelating agents, and inert gases. Suitable formualtion aids, carriers, other expients, and methods of formulating pharmaceutical compositions are disclosed in *Remington's Pharmaceutical Sciences*, 14th Ed., Mack Publishing Co., 1970, particularly Part VIII, "Pharmaceutical Preparations and Their Manufacture", pages 1461–1762, the relevant disclosures of which are incorporated herein by reference.

The attachment of a PRO to a Tat-derived transport polypeptide at to produce a Tat-PRO conjugate can be effected by any means that produces a covalent link between the PRO and Tat polypeptide, which is sufficiently stable to withstand the conditions used, and which does not alter the function of either the PRO or the Tat polypeptide. For example, recombinant techniques can be used to covalently attach a Tat-derived transport polypeptide to a PRO, such as by joining a gene coding for the PRO with a gene coding for a Tat polypeptide, and introducing the resulting gene construct into a cell capable of expressing the conjugate (genetic fusion). Alternatively, the two separate nucleotide sequences for the PRO and the Tat polypeptide can be expressed separately in a cell or can be synthesized chemically and subsequently joined, using known techniques. Alternatively, the Tat-PRO conjugate molecule can be synthesized chemically as a single amino acid sequence (i.e., one in which both constituents are present). suitable methods of linking a polypeptide to a Tat-derived polypeptide are disclosed by Frankel, et al. U.S. Pat. No. 6,316,003, the relevant disclosures of which are incorporated herein by reference.

The proline-rich oligopeptide angiogenesis inhibitors, and pharmaceutical compositions containing the inhibitors, can be packaged in suitably sterilized bottles or vials, either in multi-dose or in unit dosage forms. The containers are preferably hermetically sealed after being filled with an oligopeptide preparation. Preferably, the oligopeptides are packaged in a container having a label affixed thereto, which label identifies the inhibitor, and bears a notice in a form prescribed by a government agency such as the United States Food and Drug Administration, reflecting approval of the inhibitor under appropriate laws, dosage information, and the like. The label preferably contains information about the composition that is useful to a health care professional administering the composition to a patient. The package also preferably contains printed informational materials relating to the administration of the composition, instructions, indications, and any necessary required warnings.

Materials and Methods.

Cell Cultures. Human microvascular endothelial cells (HMEC-1 cells), were maintained and passaged in endothelial growth medium (EGM; Clonetics, San Diego, Calif.) supplemented with an additional 8% fetal bovine serum (FBS) (Gemini, Irvine Calif.) to obtain a final concentration of about 10%. For some experiments, cells were transferred to endothelial basal medium (EBM) supplemented with 0.2% FBS (Clonetics). Human umbilical vein endothelial cells (HUVECs) were purchased from Clonetics (San Diego, Calif.) and maintained in EGM media (Clonetics) supplemented to a final concentration of about 10% fetal bovine serum (FBS). Cells were maintained at about 37° C. in a humidified incubator containing about 7% by volume carbon dioxide.

Reagents. Type I rat tail collagen was obtained from Upstate Biotechnology (Lake Success, N.Y.) and recombinant bFGF was purchased from Collaborative Biomedical Products (Becton Dickinson Labware, Bedford, Mass.). Recombinant VEGF was purchased from Genetech (South San Francisco, Calif.). 10× medium 199 (M199, M0650), and PMA, were obtained from Sigma Chemical Co. (St. Louis, Mo.). ITS (insulin, transferrin, and selenium-A) and trypsin, and were purchased from Gibco-BRL (Gaithersburg, Md.). All peptides specifically referred to herein as SEQ ID NOS: 2 through 5 were synthesized by the Scripps peptide synthesis facility by standard FMOC chemistry. Additionally, fluorescent-tagged and N-terminal methionine substituted versions of selected polypeptides were synthesized by labeling the N-terminus with fluorescein isothiocyanate (FITC).

Affinity Chromatography. PRO or control peptides containing an N-terminal cysteine were dissolved in about 1 ml of coupling buffer (50 mM tris pH 8.0, 5 mM EDTA) and about 0.5 ml at about 3 mg/ml peptide added to about 2 ml of activated thiol-Sepharose (Pharmacia). Samples were incubated at a temperature of about 4° C. overnight with 1% β-mercaptoethanol added to block unreacted sites. Beads were rinsed and stored at a temperature of about 4° C. Endothelial cell cultures in 15 cm dishes were extracted in about 1.0 ml of cold (about 4° C.), lysis buffer (20 mM pH 7.4 sodium phosphate, 100 mM NaCl, 1% Triton X-100, 10 mM NaF, 2 mM EDTA, 1 mM sodium orthovanadate, 1 mM PMSF, 10 µg/ml each of leupeptin and aprotinin). The extracts were centrifuged for about 10 minutes at top speed in a microfuge and the supernatants were then removed. A 0.5 ml sample of each extract was incubated with about 10 µl of packed beads for about 1 hour, with rotation at a temperature of about 4° C. The beads were rinsed with lysis buffer (about 4×0.5 ml) and dissolved in SDS sample buffer (about 0.04 ml). Samples were analyzed by SDS PAGE on 10% gels and immunoblotting with anti-NCK (Santa Cruz) and HRP-protein A as secondary, and then were developed and detected using enhanced chemiluminescence (ECL kit, Amersham).

Microscopy. To assay migration, HMEC-1 cells were treated with various concentrations of either PRO polypeptide or mutant peptide prior to plating. Cells were plated on coverslips coated with about 2 µg/ml of fibronectin (FN). Dishes containing coverslips were prepared as described by Kiosses et al., and maintained at a temperature of about 37° C., under an atmosphere containing about 5% carbon dioxide as described by Schwartz, J. *Cell Biol.*, 1993, 120: 1003–1010. The cells were viewed with a Nikon DiaPhot Microscope equipped with a SenSys cooled CCD video camera linked to a Silicon Graphics workstation running the Inovision ISEE software program. At the end of the experiment, images of each cell were outlined and the centroid (cell center) calculated. Displacement of the centroid was then used to determine movement of the cell over time. Statistical analysis was performed using Microsoft EXCEL statistics software. Approximately 50 cells were filmed and tracked per experiment, with at least 3 independent experiments for both the PRO and the mutant peptide. Results were expressed as means±standard error of the mean. The Students t-test was used to determine whether the observed differences were statistically significant (p=0.05).

To detect entry of peptides into cells, the cells were exposed to FITC-tagged versions of the polypeptides and were fixed for about 10 minutes in a 2% formaldehyde solution (Polysciences) in phosphate buffered saline (PBS), and then washed twice in about 2 ml of PBS and mounted in Immunofluore mounting medium (ICN Immunobiologicals). Slides were viewed using a BioRad 1024 MRC Scanning Confocal Microscope.

Contractility. To visualize cell contractility, flexible rubber substrates were generated as described by Bussolino et al., *J. Biol. Chem.*, 1989, 264:18284–18287. Briefly, silicone rubber (polydimethylsiloxane), having a viscosity of about 10000 centistokes (Dow Corning Co.) was applied to the coverslip at the bottom of 35 mm tissue culture dishes and coated with a thin layer of gold-palladium using a Hummer VI sputter coater, which polymerized a thin layer of silicon rubber. The surface was additionally coated with about 2 µg/ml of fibronectin (FN). Treated and un-treated endothelial cells were plated on the rubber substrate and allowed to adhere. Cells that had wrinkled the substrate beneath were visualized for about 4 hours and then scored by time-lapse phase contrast microscopy. Following this period, the cells were treated with Cytochalasin D (about 1 µg/ml) (Molecular Probes) to release all wrinkles that were due to actin-dependent cell tension.

Formation of Three-dimensional Collagen Gels. Collagen gels were formed by mixing ice-cold gelation solution (10× M199, $H_2O$, 0.53 mol/L $NaHCO_3$, 200 mmol/L L-glutamine, type I collagen, 0.1 mol/L NaOH; 100:27.7: 50:10:750:62.5 by volume) with cells in 1×-basal medium at a concentration of about $3 \times 10^6$ cells/ml at a ratio of about 4 volumes of gelation solution to about 1 volume of cells by the method of Yang et al. *Am. J. Pathol.*, 1999, 155:887–885 (hereinafter "Yang et al."). The gels were allowed to form by incubation in a $CO_2$-free incubator at a temperature of about 37° C. for about 30–60 minutes. The gels were overlaid with 1× basal medium consisting of M199 supplemented with 1% FBS, 1× ITS, 2 mmol/L L-glutamine, 50 µg/ml ascorbic acid, 26.5 mmol/L $NaHCO_3$, 100 U/ml penicillin, 100 U/ml streptomycin and 40 ng/ml bFGF, 40 ng/ml VEGF, and 80 mmol/L PMA. At the end of the experiment, the medium was aspirated and the gels were fixed in a 3.7% formaldehyde solution. Photographs of the fixed gels were taken on a Nikon Eclipse TE300 inverted phase microscope using Hoffmann modulation contrast optics and a Polaroid digital microscope camera linked to a G4 using the Improvision software package running OpenLab version 2.2.5. In some experiments, fixed cells were stained for about 30 minutes with about 0.04% crystal violet in about 2% methanol and imaged on a Nikon DiaPhot Microscope equipped with a SenSys cooled CCD video camera linked to a Silicon Graphics workstation running the Inovision ISEE software program. Assays were performed using 48-well plates with n=3 wells for each experimental manipulation, and all experiments were repeated at least three times.

Quantification of Tube Formation. Each gel was examined on a Nikon TE300 microscope equipped with Hoffman modulation optics and a cooled CCD camera (Optronics, Technical Instruments, San Francisco, Calif.) by the method of Yang et al., 1999. Four fields, separated by 100-unit increments were imaged using OpenLab, and the data were imported as TIFF files into Inovisions ISEE software program. The total length of each tube or the long axis of single cells or groups of adjacent cells was measured, and the raw data was imported into a Microsoft Excel spread sheet. The mean tube length was determined for each well, followed by determination of the mean data and SEM for each experimental group.

Chick Cam Assays. In vivo angiogenesis assays were performed essentially as previously described by Brooks, et al., *Cell*, 1994, 79:1157–1164, the relevant disclosures of which are incorporated herein by reference. Filter discs saturated with 1.0 ug/ml bFGF were placed on the chorioallantoic membranes (CAMs) of 10-day-old chicken embryos, immediately followed by daily topical addition of either a PRO inhibitory peptide (20 µgs) or a control peptide (20 µs) in 20 µl of fibroblast growth medium (FGM). After 72 hours, the filter discs and associated CAM tissue were harvested and quantified. Angiogenesis was assessed as the number of visible blood vessel branch points within the defined area of the filter discs. At least 20 CAMs were used for each treatment.

EXAMPLE 1

Preparation of a Tat-PRO Conjugate

A PRO comprising 13 residues from the first proline-rich domain of PAK1, having the amino acid sequence of SEQ ID NO: 2, was fused to a HIV Tat protein polybasic sequence (SEQ ID NO: 3) to produce a Tat-PRO conjugate having the amino acid sequence of SEQ ID NO: 4 (FIG. 1) by the methods described above. A control peptide having SEQ ID NO: 5 was also prepared, in which the first two prolines of SEQ ID NO: 4, critical for SH3 binding, were replaced by the amino acids A and G respectively. Two additional sets of peptides were synthesized, one set with an N-terminal fluorescein group (FITC) to allow visualization and another lacking the Tat sequence (SEQ ID NO: 3) but with a C-terminal cysteine for coupling to agarose.

Figure 2:
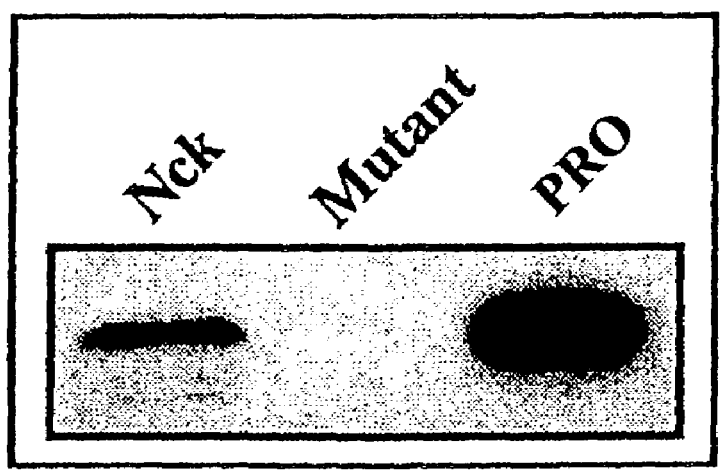
FIG. 2 depicts lysates of endothelial cells (left) and endothelial cells that were incubated with the Tat-PRO (right) and control peptide (center) shown in FIG. 1, analyzed by Western blotting with anti-Nck.

To test binding specificity, detergent extracts of human endothelial cells were incubated with peptide-agarose, followed by washing and analysis by western blotting with anti-Nck. We observed that the PRO inhibitor (SEQ ID NO: 4) of the present invention bound Nck from the lysates, whereas no detectable Nck was bound to the control peptide. This result confirms the ability of this proline-rich sequence of the inhibitor to specifically bind Nck, presumably through its SH3 domain. To test the ability of Tat protein fusions to enter cells, the fluorescent derivatives were incubated with endothelial cell monolayers, washed and fixed. Some heterogeneity was observed in the intensity of labeling, but by about 20 minutes the majority of the cells showed strong cytoplasmic labeling with the fluoresceinated (FITC) peptides. Some labeling of the matrix and nucleus was also noted. FIG. 2 shows Western blots (with anti-Nck) of lysates of endothelial cells (left) and endothelial cells that were incubated with the Tat-PRO (right) and control peptide (center). These results suggest that the Tat-PRO fusion protein can be useful for testing function in live cells.

EXAMPLE 2

Migration and Contractility Assay of the Inhibitor of Example 1

Figure 3:
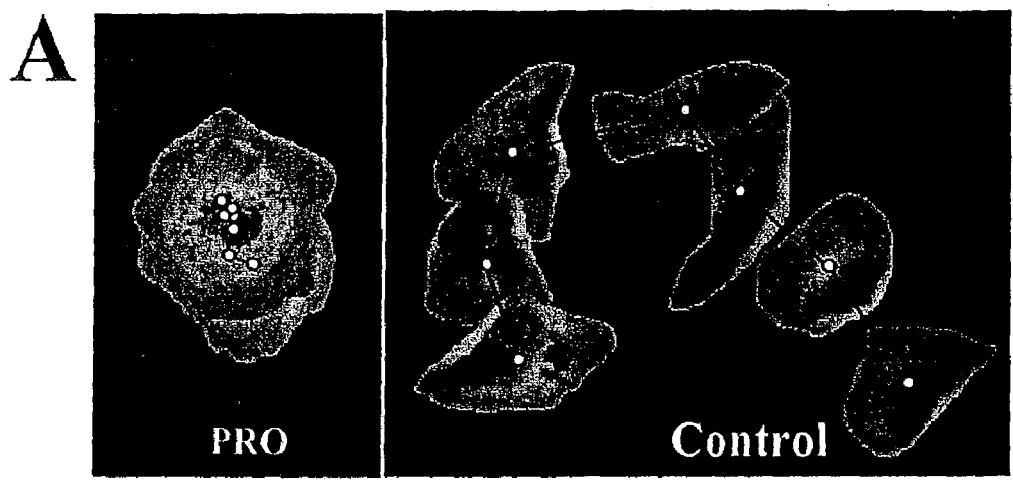
FIG. 3A illustrates human endothelial cells that were incubated with or without the Tat-PRO and control peptide shown in FIG. 1, wherein random cell migration was followed by time lapse imaging, demonstrating that cells treated with the Tat-PRO inhibitor displayed significantly reduced migration relative to cells treated with the control polypeptide.
FIG. 3B graphically demonstrates that the rate of migration of endothelial cells treated with the Tat-PRO of FIG. 1 displayed markedly decreased migration rates compared to untreated controls cells and cells treated with the control polypeptide.
FIG. 3C demonstrates the dependence of migration rate on the concentration of the Tat-PRO of FIG. 1.
Figure 3:
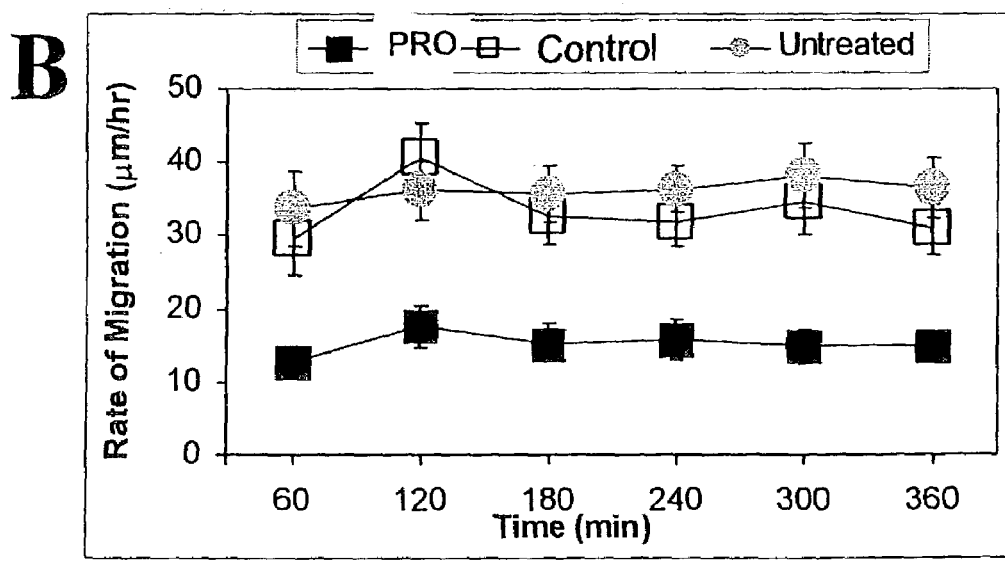
Figure 3:
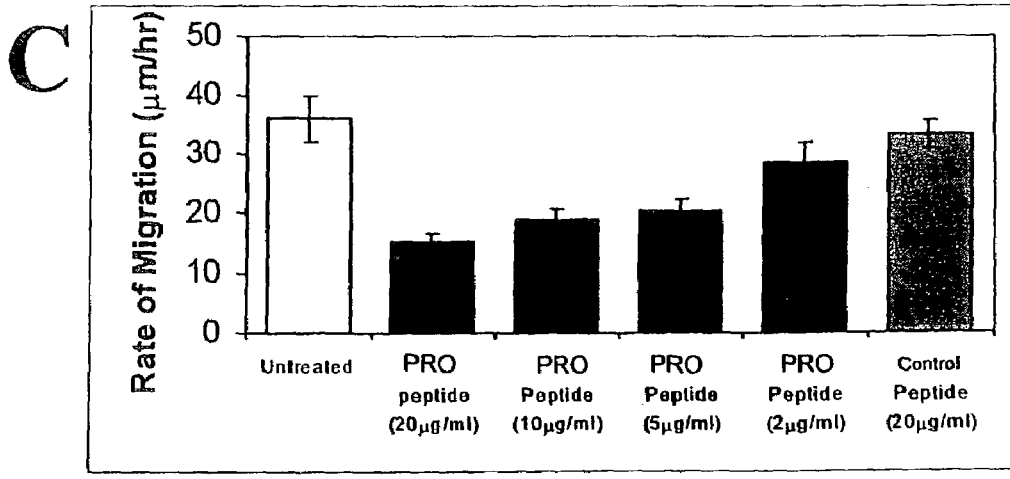

To test whether these PRO angiogenesis inhibitors influenced endothelial cell behavior similar to over expression of the longer PAK constructs, endothelial cells on coverslips were incubated with the Tat-PRO conjugate inhibitor (SEQ ID NO: 4) and the control peptide (SEQ ID NO: 5) and time lapse imaging was carried out. Analysis of these images showed that endothelial cells in the presence of about 10 µM of the Tat-PRO inhibitor migrated at a substantially slower rate than the control, and that the control peptide had no significant effect on migration (FIG. 3A). Endothelial cell migration rates were essentially constant over the time course of the experiment, which argues against toxicity or other deleterious effects (FIG. 3B). Analysis of different concentrations of the PRO angiogenesis inhibitor showed that the half-maximal inhibition was observed at approximately 5 µg/ml (2 µM), and was nearly maximal at 20 µg/ml (FIG. 3C).

Figure 4:
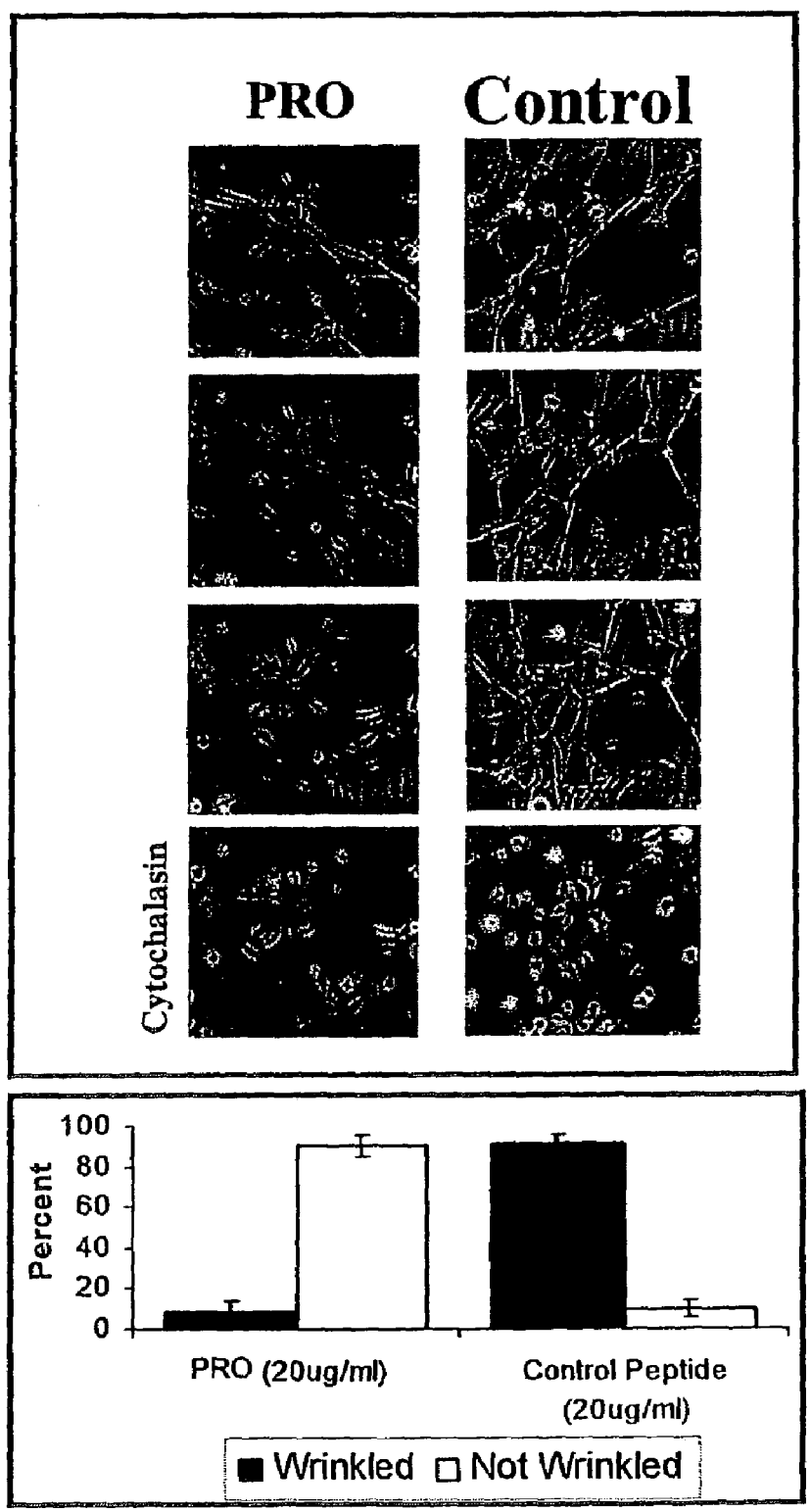
FIG. 4 illustrates reduction in contractility of endothelial cells treated with the Tat-PRO of FIG. 1 relative to the contractility of endothelial cells treated with the non-inhibitory control protein.

To examine effects on contractility, cells were plated on elastic substrata, as described above, that can be pulled into wrinkles by cell-generated forces. Cells plated on these surfaces initially induced wrinkles, indicating the application of contractile forces to the substratum. Addition of PRO (SEQ ID NO: 4) of Example 1 at about 10 µM concentration caused a release of wrinkles, indicating a decrease in cell-generated tension (FIG. 4A), whereas the control peptide (SEQ ID NO: 5) had no effect. Quantification of these results indicated a consistent and significant inhibition of contractility induced by the PRO inhibitor (FIG. 4B). Taken together, these data show that soluble Tat-PRO fusion peptides exert effects on cells that are essentially identical to the previously examined dominant negative PAK expression constructs of Kiosses et al.

EXAMPLE 3

In Vitro Tube Formation Assay

Figure 5:
FIG. 5A illustrates the inhibition of endothelial cell tube formation in a 3D collagen matrix for cells treated with the Tat-PRO of FIG. 1 relative to cells treated with the control polypeptide.
FIG. 5B graphically depicts the decreased average vessel (tube) length of the Tat-PRO-treated cells of FIG. 5A relative to the control cells.
Figure 5:
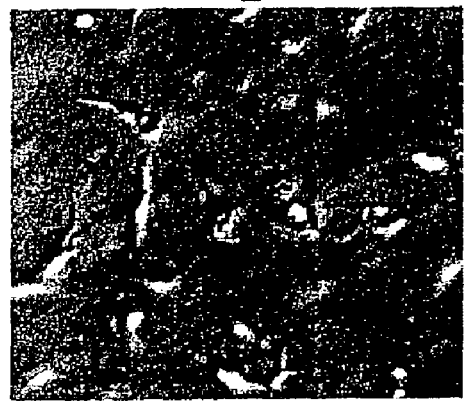
Figure 5:
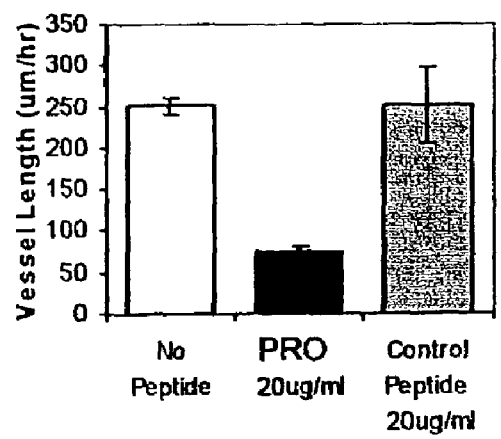

As an initial test of the PRO effect on endothelial cell behavior in 3-dimensional matrices, in vitro tube formation assays in matrigel were carried out. Human umbilical vein endothelial cells (HUVECs) in matrigel in the presence of bFGF, VEGF and phorbol ester (PMA) aligned and formed endothelial tubes with lumens over approximately 2 days. Assays were set up in the presence of several concentrations of the PRO (SEQ ID NO: 4) or control peptide (SEQ ID NO: 5) of Example 1, and examined at about 48 hours. Tube formation was quantitated by determining the length of endothelial cell tubes. As shown in FIG. 5, the PRO significantly inhibited tube formation in this system. Morphology of individual cells was not noticeably perturbed, nor was cell number greatly altered, ruling out toxicity or general disruption of the cytoskeleton under these conditions. These data demonstrate that PRO can inhibit contractility and migration, both of which are necessary for the formation of multicellular structures in 3D matrix.

EXAMPLE 4

In Vivo Angiogenesis Assay

Figure 6:
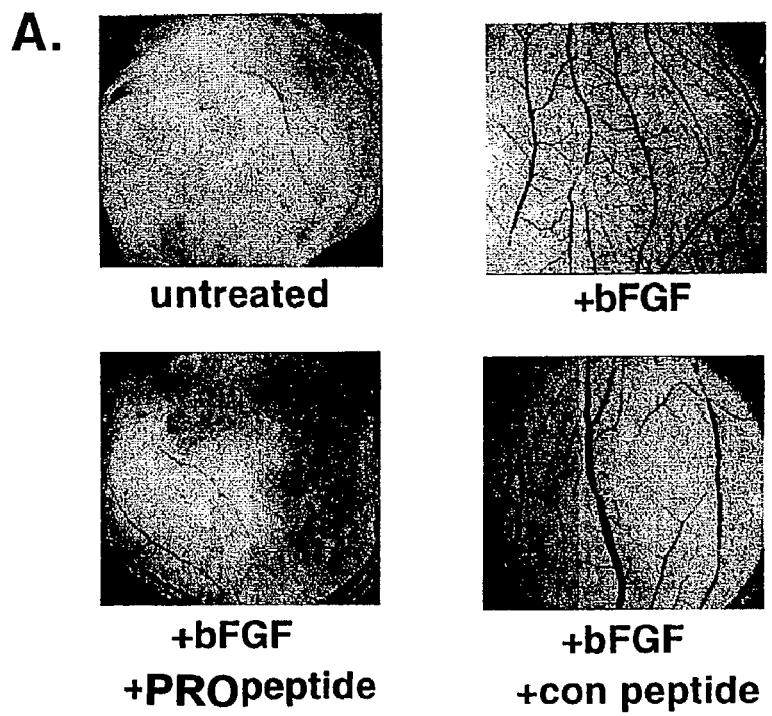
FIG. 6A depicts photomicrographs showing reduced vascularization (angiogenesis inhibition) in chick CAMs treated with the inventive Tat-PRO of FIG. 1 relative to a CAM treated with the control polypeptide.
FIG. 6B graphically illustrates the number of vascular branch points in the CAMs depicted in FIG. 6A.
Figure 6:
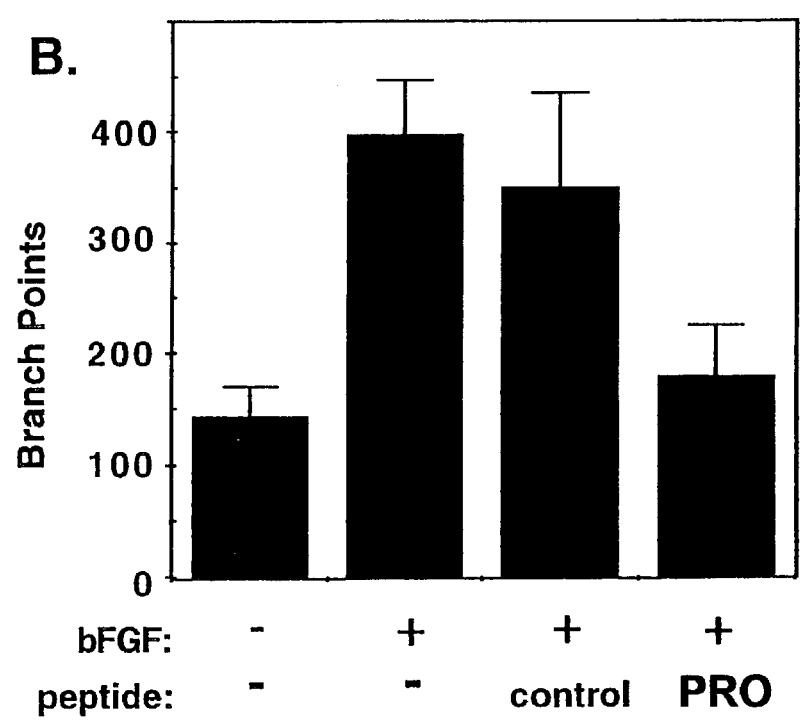

A chick CAM model, in which filters containing bFGF are placed on the chorioallantoic membrane (CAM) of developing chick embryos was utilized to demonstrate the effectiveness of the PRO (SEQ ID NO: 4) of Example 1 to inhibit angiogenesis. New blood vessels invade the filter dishes within 2–5 days, and angiogenesis can be readily detected. Filters without any additions, with control or with the PRO compound of Example 1 were implanted and examined 3 days later. FIG. 6 shows that the PRO substantially inhibited angiogenesis compared to untreated filters, and that the control peptide (SEQ ID NO: 5) had essentially no effect. These results show that a PRO inhibitor can block bFGF-induced angiogenesis in vivo.

The inventive proline-rich oligopeptide-based angiogenesis inhibitor is a synthetic peptide covering a first proline-rich domain of PAK1 which exhibits specific binding to Nck. Coupling a proline-rich PAK binding sequence to a region from the HIV Tat protein promotes its rapid entry into endothelial cells where it exerts dominant negative effects that are essentially indistinguishable from those of over-expressed full length dominant negative PAK. The peptide-based inhibitors of the present invention, therefore, provide the angiogenesis inhibiting effectiveness of dominant negative PAK in systems that are not readily amenable to transfection.

Analysis of endothelial cells in vitro in a 3-dimensional extracellular matrix showed that the inventive PRO markedly blocked formation of extended multicellular structures without apparent deleterious effects on single cell morphology or number. Yang et al. reported that these structures contain lumens and therefore resemble capillary tubes in vivo. The effect of the PRO is therefore consistent with inhibition of cell migration. Analysis of angiogenesis in a chick CAM model also revealed significant inhibition by the PRO peptide. Taken together, these results demonstrate that PRO inhibits endothelial cell migration and angiogenesis, most likely via effects on the cytoskeleton.

Numerous variations and modifications of the embodiments described above may be effected without departing from the spirit and scope of the novel features of the invention. No limitations with respect to the specific embodiments illustrated herein are intended or should be inferred. The appended claims are intended to cover all such modifications as fall within the scope of the claims.

We claim:

1. A oligopeptide including a proline-rich segment having a total of 7 to 20 amino acid residues and including at least one amino acid sequence PPXPP (SEQ ID NO: 1), covalently bound to a transport molecule segment; wherein X is an amino acid residue selected from the group consisting of A, G, S, T, L and M; the oligopeptide having angiogenesis inhibiting activity.

2. The oligopeptide of claim 1 wherein the transport molecule is covalently bound to the N-terminus of the proline-rich segment.

3. The oligopeptide of claim 1 wherein the transport molecule is a Tat-derived transport polypeptide.

4. The oligopeptide of claim 3 wherein the proline-rich segment has the amino acid sequence of SEQ ID NO: 2.

5. The oligopeptide of claim 3 wherein the Tat-derived transport polypeptide is a peptide having the amino acid sequence of SEQ ID NO: 3.

6. The oligopeptide of claim 1 wherein X is A.

7. A oligopeptide including a proline-rich segment and at least one amino acid sequence PPXPP (SEQ ID NO: 1), covalently bound to a transport molecule segment; wherein X is an amino acid residue selected from the group consisting of A, G, S, T, L and M; the oligopeptide having angiogenesis inhibiting activity and wherein the proline-rich segment has a total of 8 amino acid residues.

8. The oligopeptide of claim 7 wherein X is A.

9. An article of manufacture comprising an oligopeptide of claim 7, in a pharmaceutically acceptable carrier, packaged in a hermetically sealed, sterile container, the container having a label affixed thereto, the label bearing printed material identifying the oligopeptide and providing information useful to an individual administering said oligopeptide to a patient.

10. The article of manufacture of claim 9 wherein the oligopeptide has the amino acid sequence of SEQ ID NO: 2.

11. The article of manufacture of claim 9 wherein the oligopeptide is covalently bound, at its N-terminus, to a Tat-derived transport polypeptide.

12. The article of manufacture of claim 11 wherein the Tat-derived transport polypeptide has the amino acid sequence of SEQ ID NO: 3.

* * * * *